(12) United States Patent
Takahashi

(10) Patent No.: US 6,485,458 B1
(45) Date of Patent: Nov. 26, 2002

(54) SURGICAL INSERTION INSTRUMENT BODY HAVING A DISTENDING PORTION

(75) Inventor: Katsumi Takahashi, Koga (JP)

(73) Assignee: Johnson & Johnson Kabushiki Kaisha (JP)

( * ) Notice: Subject to any disclaimer, the term of this patent is extended or adjusted under 35 U.S.C. 154(b) by 0 days.

(21) Appl. No.: 09/491,617

(22) Filed: Jan. 26, 2000

(30) Foreign Application Priority Data

Jan. 27, 1999 (JP) .......................................... 11-019009

(51) Int. Cl.[7] .............................................. A61M 29/00
(52) U.S. Cl. ........................ 604/104; 604/113; 604/531; 606/198
(58) Field of Search ................................ 604/104–109, 604/13, 264, 523, 525, 528, 530–532, 534–536, 96.01; 606/191, 197–199; 600/433–435

(56) References Cited

U.S. PATENT DOCUMENTS

| | | | | |
|---|---|---|---|---|
| 5,112,310 A | * | 5/1992 | Grobe | 604/103.03 |
| 5,409,460 A | * | 4/1995 | Krumme | 604/107 |
| 5,456,667 A | * | 10/1995 | Ham et al. | 604/104 |
| 5,707,362 A | * | 1/1998 | Yoon | 604/164.03 |
| 5,730,698 A | * | 3/1998 | Fischell et al. | 600/3 |
| 5,885,258 A | * | 3/1999 | Sachdeva et al. | 600/141 |
| 6,152,899 A | * | 11/2000 | Farley et al. | 604/106 |
| 6,270,490 B1 | * | 8/2001 | Hahnen | 604/104 |
| 6,338,727 B1 | * | 1/2002 | Noda et al. | 604/113 |

* cited by examiner

Primary Examiner—Brian L. Casler
Assistant Examiner—LoAn H. Thanh

(57) ABSTRACT

An insertion instrument body includes a longitudinal metallic core portion, a distending portion and a power supply means. The metallic core portion is inserted into a lumen such as a blood vessel. The distending portion is fixed to an outer face of the metallic core portion. The power supply means heats the distending portion above a transforming temperature. The distending portion includes a cylindrical portion which is mountable on the metallic core portion; and a plurality of rod-shaped portions which are integrally formed in the cylindrical portion and which are made of a shape-memory material. The rod-shaped portion returns to an original shape by displacing in an intersecting direction with respect to a longitudinal direction of the metallic core portion. An electrical insulating layer is formed on an outer surface of the metallic core portion, and the electrical insulating layer is covered with a flexible sleeve. A power supply means is constituted of the metallic core portion, the flexible sleeve, a power source and a switch.

13 Claims, 7 Drawing Sheets

SURGICAL INSERTION INSTRUMENT BODY HAVING A DISTENDING PORTION

RELATED APPLICATION

This application claims priority from Japanese Application Serial No. 19009/99, filed Jan. 27, 1999.

FIELD OF THE INVENTION

The present invention relates to an insertion instrument body used for a medical treatment for distending a narrow portion in a lumen such as a blood vessel of a patient, and to a method for manufacturing the same.

BACKGROUND OF THE INVENTION

In a conventional treatment for curing a heart disease such as a cardiac angina and a myocardial infarct, a patient is subjected to a series of procedures. The procedures include the steps of inserting a balloon-tip catheter into a narrow portion in a coronary artery in a heart of a patient in vivo, inflating a balloon which is mounted on a distal end of the balloon-tip catheter to distend the narrow portion, and pulling the catheter. A guide-wire is known as an instrument used for introducing the balloon-tip catheter into an inner space of the very thin blood vessel, such as shown in the FIGS. 12 and 13.

FIG. 12 is a general front view showing a distal end of a conventional guide-wire. FIGS. 13(a) and 13(b) are general front views showing a state that a balloon-tip catheter is introduced into a blood vessel by using the conventional guide-wire shown in the FIG. 12, and are partially cross sectional views. A reference numeral 1 in the FIG. 12 denotes a distal end of the guide-wire, and a reference numeral 2 denotes a flexible metallic core portion. An outer face of the metallic core portion 2 is covered with a not-shown sleeve as a coating formed by spraying a high molecular resin such a polytetrafluoroethylene, namely PTFE and so on. A coil is formed to surround the distal end of the metallic core portion 2 to form a coil spring portion 3. Since X-rays are not able to pass through the coil spring portion 3, the distal end of the guide-wire 1 is clearly observed by the X-ray images. Therefore, a position of the distal end of the guide-wire 1 can be exactly controlled within the patient body by X-ray images.

As illustrated in the FIG. 13(a), since the guide-wire 1 can proceed deeply in a blood vessel 4 such as the coronary artery of the heart in vivo, a balloon-tip catheter 5 can be easily introduced into a narrow portion 6 of the blood vessel 4 by using the metallic core portion 2 as a guide instrument. In the narrow portion 6 of the blood vessel 4, an inner space can be produced by increasing a balloon 7 of the balloon-tip catheter 5 as illustrated in the FIG. 13(b).

Sometimes, the narrow portion 6 in the blood vessel 4 is almost blocked up so that the inner diameter becomes so small that the distal end of the guide-wire 1 can narrowly be inserted into the narrow portion 6. In this case, emergency procedures are taken so that the inner diameter of the narrow portion 6 in the blood vessel 4 is gradually distended. The procedures include the steps of preparing a plurality of catheters having different outer diameters; and inserting catheters one by one in ascending order of outer diameter into the narrow portion 6 along the guide-wire 1 which has already been inserted thereinto. By using a plurality of catheters, time required for such an operation program is prolonged and the expense is increased. In case that the catheters cannot be introduced into the blood vessel, open-heart surgery must be performed, increasing trauma to the patient.

In the narrow portion 6 of the above blood vessel 4, an inner space is obtained by means of the metallic core portion 2 of the guide-wire 1. It is therefore required an insertion instrument body which can promptly perform the distention of the narrow portion 6 in order to maintain the inner space above be developed.

An object of the present invention is to provide an insertion instrument body and a method for manufacturing the same, the insertion instrument body able to securely distend a narrow portion of the blood vessel being almost blocked up.

SUMMARY OF THE INVENTION

According to one aspect of the present invention, there is provided an insertion instrument body to be inserted into a lumen in vivo, including: a longitudinal base portion insertable into the lumen in vivo; a distending portion distending the lumen in vivo and arranged on an outer face of the distal end of the base portion, wherein the distending portion extends in a longitudinal direction of the base portion and is at least partially formed of a shape-memory material which displaces in an intersecting direction with respect to the longitudinal direction of the base portion at a temperature above a transforming temperature of the shape-memory material and returns to an original shape; and a power supply means for heating the distending portion to a temperature above the transforming temperature.

Here, "insertion instrument body" means an instrument for distending an inner space of lumen, tubes and blood vessels, and more concretely includes a surgery instrument such as a guide-wire, a catheter and so on with a distending portion made of a shape-memory material. In this specification, "guide-wire" means a thin guide member to be inserted in the lumen prior to the catheter. "Catheter" means a cylindrical, hollow member having a radius slightly greater than that of the guide-wire, and being able to inject or suck liquid. Moreover, the catheter can be used to secure an inner space within a route such as a blood vessel. "Shape-memory material" means a high molecular weight material such as a metal, resin or the like which has a shape-memory effect (SME) and a superelastic effect (SE). Although SE is taken at the room temperature lower than a transforming temperature, SME is taken at a temperature higher than the transforming temperature. "SME" means a property that causes the rigidity of the shape-memory material to be increased so that the material returns to a memorized original shape. Further, the arrangement of the distending portion on the outer face of the distal end of the longitudinal base portion described above includes two embodiments. In the first embodiment, the distending portion includes a cylindrical body having an inner space to which the base portion is insertable, and a rod-shaped portion formed to be integrally with the cylindrical body. Moreover, the cylindrical body is mounted on the distal end of the longitudinal base portion so as to cause an inner wall of the cylindrical body to come into contact with the outer face of the base portion. In the second embodiment, the distending portion does not include the cylindrical body as described above, and includes only the rod-shaped portion displaceable as a result of the shape-memory effect. The distal end of the base portion consists of some continuous parts having different outer sizes such as different outer radii and so on. Therefore, the outer face of the base portion at an optionally selective position is defined by the outer size such as an outer radius at the optionally selective position in the distal end thereof.

According to another aspect of the present invention, there is provided a method for manufacturing an insertion instrument body to be inserted into a lumen in vivo, comprising the steps of: preparing a longitudinal base portion insertable into the lumen in vivo; forming a groove extending approximately in an axial direction of a cylindrical body on a part of an outer surface of said cylindrical body to produce at least one rod-shaped portion on the outer surface of said cylindrical body, wherein said cylindrical body is formed of a shape-memory material and is mountable on said base portion; providing a shape-memory to said rod-shaped portion to define the total of said cylindrical body as an distending portion for distending the lumen in vivo, wherein the shape-memory is defined by displacing said rod-shaped portion in an intersecting direction with respect to the longitudinal direction of said base portion at a temperature above a transforming temperature of the shape-memory material when said rod-shaped portion is fixed to an outer face of the distal end of said base portion so that said rod-shaped portion approximately extends along a longitudinal direction of said base portion and returns to an original shape; fixing said cylindrical body to the outer face of the distal end of said base portion; and connecting a power supply means to at least said distending portion, said power supply means heating said distending portion to a temperature above the transforming temperature. This manufacturing method relates to an insertion instrument body regarding the embodiment described above. Here, the groove to be formed on the cylindrical body may be limited to only one such groove. In this case, it is possible to form one rod-shaped portion by forming one groove having a large width.

An insertion instrument body 8 includes a longitudinal metallic core portion 2, a distending portion 9 and a power supply means 10. The metallic core portion is inserted into a lumen such as a blood vessel. The distending portion 9 is fixed to an outer face of the metallic core portion 2. The power supply means 10 heats the distending portion 9 above a transforming temperature. The distending portion 9 includes a cylindrical portion 11 which is mountable on the metallic core portion 2; and a plurality of rod-shaped portions 12 which are integrally formed in the cylindrical portion 11 and which are made of a shape-memory material. The rod-shaped portion 12 returns to an original shape by displacing in an intersecting direction with respect to a longitudinal direction of the metallic core portion 2. An electrical insulating layer 21 is formed on an outer surface of the metallic core portion 2, and the electrical insulating layer 21 is covered with a flexible sleeve 22. A power supply means 10 is constituted of the metallic core portion 2, the flexible sleeve 22, a power source 24 and a switch 25.

According to further another aspect of the present invention, there is provided a method for manufacturing an insertion instrument body to be inserted a lumen in vivo, comprising the steps of: preparing a longitudinal base portion insertable into the lumen in vivo; preparing at least one rodshaped body which consists of a shape-memory material; providing a shape-memory to said rod-shaped body to define the total of said cylindrical body as a distending portion for distending the lumen in vivo, wherein the shape-memory is defined by displacing said rod-shaped portion in an intersecting direction with respect to the longitudinal direction of said base portion at a temperature above a transforming temperature of the shape-memory material when said rod-shaped body is fixed to an outer face of the distal end of said base portion so that said rod-shaped portion approximately extends along a longitudinal direction of said base portion and returns to an original shape; fixing said distending portion to the outer face of the distal end of said base portion so said distending portion approximately extends in the longitudinal direction of said base portion; and connecting a power supply means to at least said distending portion, said power supply means heating said distending portion to a temperature above the transforming temperature.

This manufacturing method relates to an insertion instrument body regarding the second embodiment as described above. Here, the power supply means constitutes an electric circuit including the distending portion. The electric circuit can optionally include the longitudinal base portion. When the electric circuit includes both the distending portion and the base portion, the distending portion must be electrically insulated from the base portion. The rod-shaped portion or member means a thin, longitudinal portion or member such as thin plate, wire and so on. The thickness of the rod-shaped portion or member is suitably determined in view of the outer size of the base portion.

DESCRIPTION OF THE DRAWINGS

Hereinafter, embodiments of an insertion instrument body according to the invention will be explained in detail with reference to the accompanying drawings.

DETAILED DESCRIPTION OF THE INVENTION

Figure 1A:
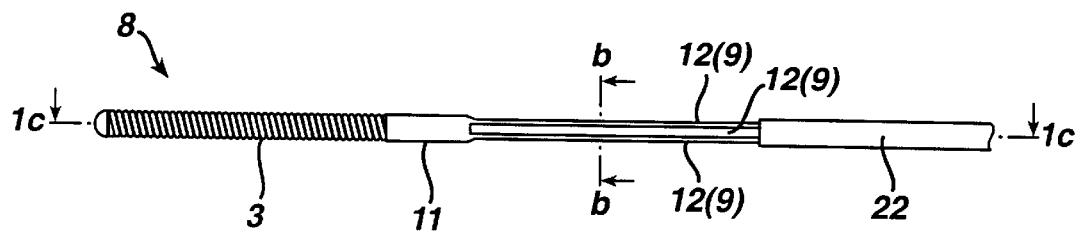
FIG. 1(a) is a front view showing a distal end of guide-wire as a first embodiment according to an insertion instrument of the present invention.
Figure 1B:
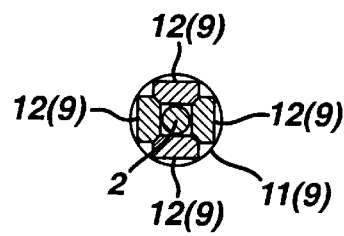
FIG. 1(b) is an enlarged cross sectional view taken along the line b—b of FIG. 1(a)
Figure 1C:
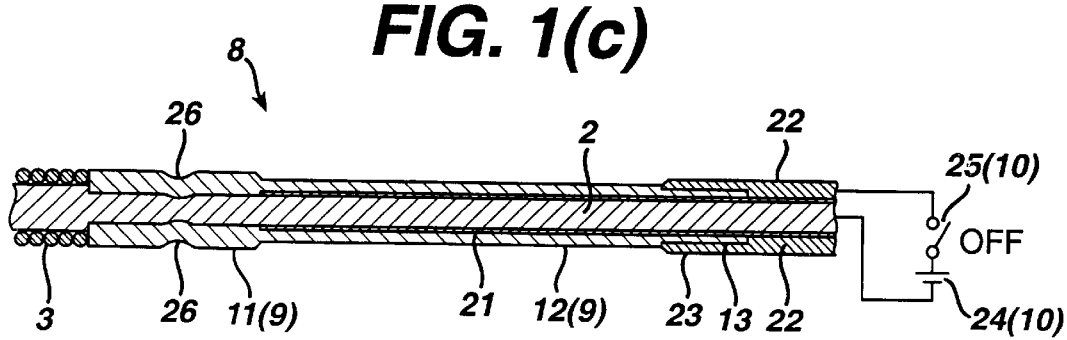
FIG. 1(c) is an enlarged cross sectional view taken along the line c—c of FIG. 1(b)
Figure 12:
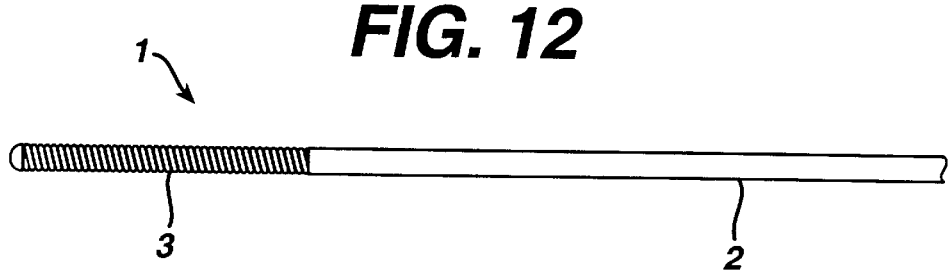
FIG. 12 is a general front view showing a distal end of a conventional guide-wire.
Figure 13A:
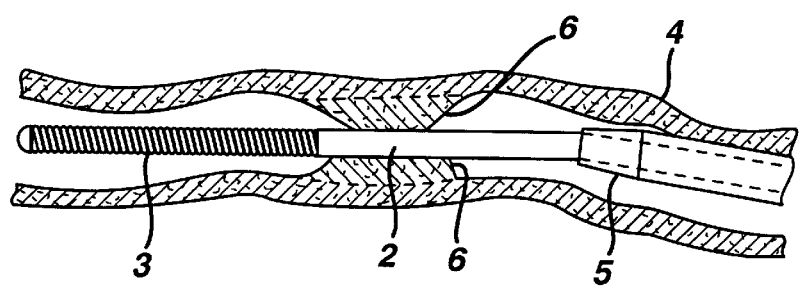
FIGS. 13(a) and 13(b) are general front views in partial cross-section showing the condition in which a balloon-tip catheter is introduced into a blood vessel by using the conventional guide-wire shown in the FIG. 12.
Figure 13B:
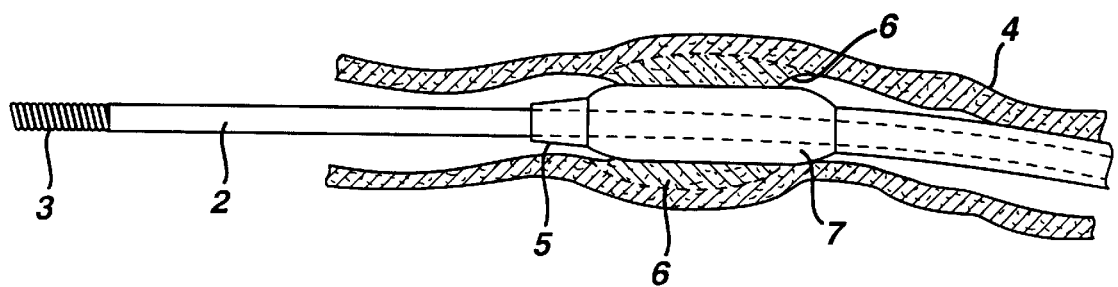

FIG. 1(a) is a front view showing a distal end of guide-wire as an embodiment 1 of an insertion instrument body according to the present invention, the FIG. 1(b) is an enlarged cross sectional view taken along the line b—b of the FIG. 1(a); and the FIG. 1(c) is an enlarged cross sectional view taken along the line c—c of the FIG. 1(b). In this embodiment, the common elements shown in both the FIGS. 1(a) to (c) and the FIGS. 12 and 13, are represented by reference numerals of the FIGS. 12 and 13.

In FIGS. 1(a) to 1(c), a reference numeral 8 designates an insertion instrument body. The insertion instrument body 8 has a metallic core portion (base portion) 2 as a primary element in the conventional insertion instrument body such as a conventional guide-wire; a distending portion 9 for distending the blood vessel 4 (lumen) in vivo to obtain a required space in the narrow portion 6 of the blood vessel 4, the distending portion 9 being arranged on an outer face of the distal end of the metallic core portion 2; and a power supply means 10 for warming the distending portion 9 at a temperature higher than the required temperature. The distending portion 9 has a cylindrical portion (cylindrical body) 11 having an inner diameter slightly greater than an outer diameter of the metallic core portion 2; and a plurality of rod-shaped portions 12 which extend straight from a peripheral portion of one end of the cylindrical portion 11 in an axial direction of the cylindrical portion 11. Here, in this embodiment, the distending portion 9 has four rod-shaped portions 12.

The rod-shaped portion 12 is a plate-like or wire-like member, and is made from the shape-memory material having an original shape which displaces outwardly in a direction along the radius of the cylindrical portion 11 at a temperature higher than a transforming temperature of the shapememory material. As shown in the FIG. 1(b), the cross section of the cylindrical portion 11 has an approximately rectangular shape, and inner apices of the rod-shaped portion 12 facing the radial center of the cylindrical portion 11 are chamfered so as not to come into contact with the neighborhood rod-shaped portions 12. The cross section of the rod-shaped portion 12 may be of a curved shape including an oval shape, a circular shape and a combination thereof, in addition to a rectangular shape.

The shape-memory material used as a constituent material for the rod-shaped portion 12 may preferably be metallic materials such as titanium-nickel alloys copper-aluminum-nickel alloys, copper-zinc alloys, and high molecular materials such as polynorbornen based polymers (trade-name: Nothorex, trade-name: Zeonshable, made by Nippon Zeon, Japan), styrene-butadiene based co-polymers (trade-name: Asmer, Japan), a polyurethane based polymer (trade-name: Diary, Japan), polyisoprene based polymers, polyester based polymers, polyolefin based polymers, acrylic based polymers, styrene-acrylic based polymer and so on. However, other shape-memory materials may also be used.

The transforming temperature of the shape-memory material should be sufficiently low to avoid a lower-temperature burn in a patient in vivo. In an ordinary surgical operation, the transforming temperature ranges between 40° C. and 60° C., a range slightly higher than a normal human body temperature, for example, 37° C., and preferably ranges between 40° C. and 50° C. In a special surgical operation requiring lower body temperature, the transforming temperature may be lower than the normal body temperature (37° C.).

In this embodiment, four rod-shaped portions 12 extend from a peripheral portion of an end of the cylindrical portion 11 as described above. In this case, at a temperature below the transforming temperature, the rod-shaped portions 12 before transformation are preferably accommodated in the form of a bundle within a space which is defined between an outer face of the distal end of the metallic core portion 2 and an outer face of the cylindrical portion 11. In other words, unless the insertion instrument body 8 is as thin as a conventional guide-wire, it cannot be close to a narrow portion of a blood vessel. In this embodiment, while the four rod-shaped portions 12 are the same as each other in shape and size, they need not be the same if they are bundled in the space below the transforming temperature.

A coating layer (not shown) is formed on a surface of the rod-shaped portion 12, of the distending portion 9, and is made from polyurethane, polyvinylpyrrolidine, and polyethylene oxide, for example. Since the coating layer is hydrophilic, it can be easily inserted into the blood vessel. An end of the rod-shaped portion 12 is thinned from an outer face thereof to form an engagement portion 13. An electrical insulating portion 21 is formed on an outer face of the longitudinal, metallic core portion 2, and the electrical insulating portion 21 is covered with a flexible sleeve 22 which is made from a conductive material. An end of the flexible sleeve 22 is also thinned from an inner face, and the thinned portion serves as an engagement portion 23 which is engaged with the engagement portion 13 of the distending portion 9 inserted in a space defined between the flexible sleeve 22 and the metallic core portion 2. An electrical circuit is constituted by a part of the metallic core portion 2, a part of the flexible sleeve 22, a power source 24 and a switch 25, and serves as a power supply means 10 controlling a temperature of the rod-shaped portion 12 made of the shape-memory material. In FIG. 1(c), since the switch 25 is opened, the electric circuit is off. Therefore, the rod-shaped portion 12 not yet warmed and is not displaced.

Figure 2A:
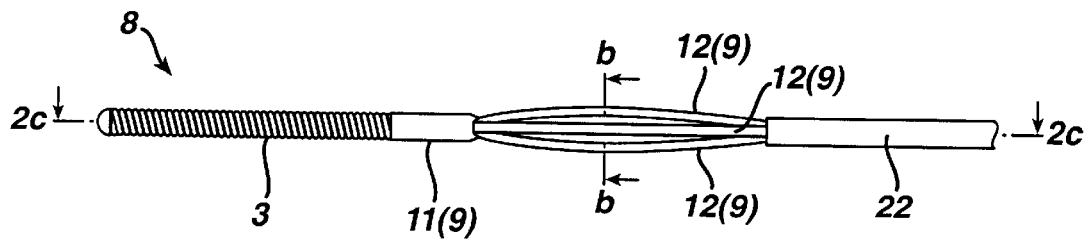
FIG. 2(a) is a front view showing an action for distending a narrow portion in a lumen in vivo by means of a distending portion of the guide-wire shown in FIG. 1(a)
Figure 2B:
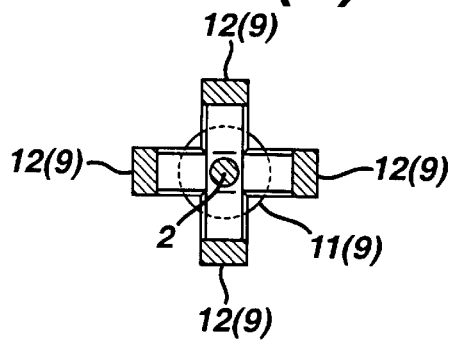
FIG. 2(b) is a cross sectional view in large taken along the line b—b of FIG. 2(a)
Figure 2C:
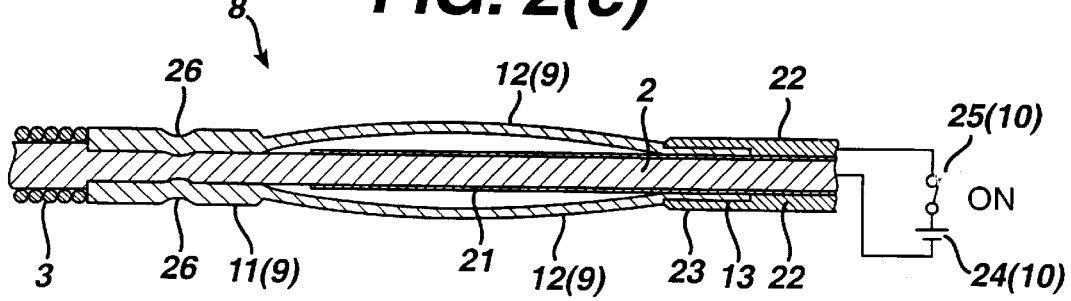
FIG. 2(c) is a cross sectional view in large taken along the line c—c of FIG. 2(b)

Since the cylindrical portion 11 of the distending portion 9 is made from the same shape-memory material as the rod-shaped portion 12, it cannot easily adhere to a portion made of a material other than the shape-memory material. Therefore, in this embodiment, the cylindrical portion 11 is fixed to the distal end of the metallic core portion 2 by caulking method. In FIG. 2(c), a reference numeral 26 denotes a recess for fixation formed by the caulking. Alternatively, the cylindrical portion 11 may be fixed to the metallic core portion 2 by a method other than a mechanical method such as caulking. For example an adhesive connecting method such as brazing, or another method such as welding or ultrasonic seizing may also be used. These methods may be also applied to connecting faces between the engagement portions 13 and 23.

The action of the rod-shaped portion 12 will be explained hereinafter with reference to FIGS. 2(a) to 2(c). The FIG. 2(a) is a front view showing an action for distending a narrow portion in a lumen in vivo by means of a distending portion of the guide-wire shown in the FIG. 1(a). The FIG.

2(b) is an enlarged cross sectional view taken along the line b—b of the FIG. 2(a). The FIG. 2(c) is an enlarged cross sectional view taken along the line c—c of the FIG. 2(b).

As shown in the FIG. 2(c), the rod-shaped portion 12 is promptly warmed above a required transforming temperature by closing the switch 25 to switch on the power supply means. As shown in the FIGS. 2(a) to 2(c), on heating, a central portion of the rod-shaped portion 12 returns to an original shape outwardly curved in a radius direction of the cylindrical portion 12. Since a space formed by the rod-shaped portion 12 reaches a radius greater than the radius of the cylindrical portion 11, this enlargement can be utilized to distend the narrow portion in the blood vessel.

The action of the distending portion for distending the narrow portion in the blood vessel will be explained hereinafter with reference to FIGS. 3(a) to 3(c). The FIGS. 3(a) to 3(c) are front views showing a series of actions for distending a narrow portion of the blood vessel by using the guide-wire shown in the FIGS. 1(a) to 1(c) and 2(a) to 2(c), and are partially cross sectional views.

Figure 3A:
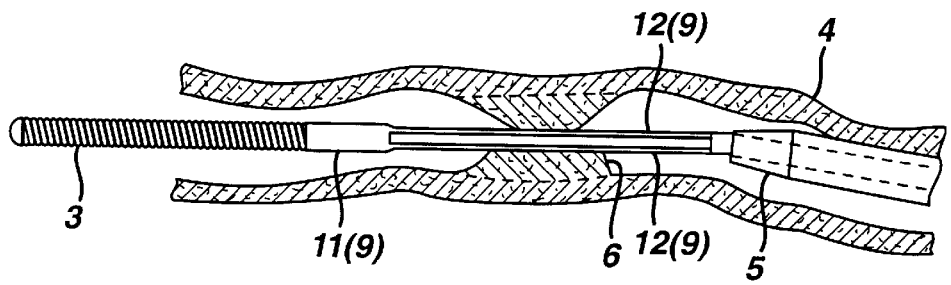
FIGS. 3(a) to 3(c) are front views in partial cross section, showing a series of actions for distending a narrow portion of blood vessel by using the guide-wire shown in FIGS. 1(a) to 1(c) and 2(a) to 2(c)

As shown in the FIG. 3(a), a coil spring portion 3 of the guide-wire 1 is inserted into the blood vessel 4. The rod-shaped portion 12 reaches the narrow portion 6 in the blood vessel 4 because the rod-shaped portion has approximately the same diameter as the coil spring portion 3. Since the outer diameter of the rod-shaped portion 12 is very small, the rod-shaped portion 12 can pass through the narrow portion 6. On the other hand, a balloon-tip catheter following the rod-shaped portion 12 inserted thereinto has an outer diameter slightly larger than that of the rod-shaped portion 12, and accordingly it is not easy for the balloon-tip catheter 5 to pass through the narrow portion 6.

Figure 3B:
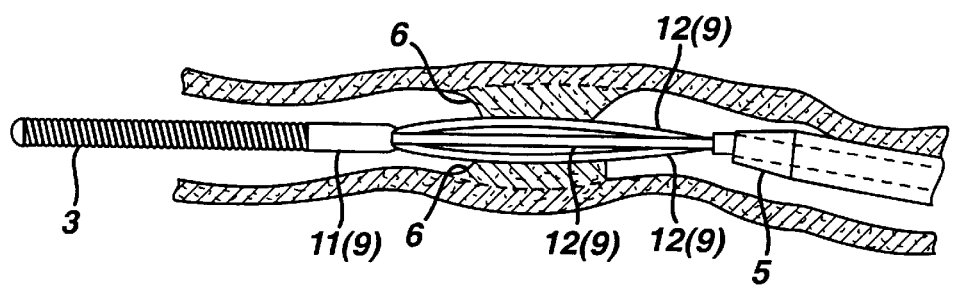
Figure 3C:
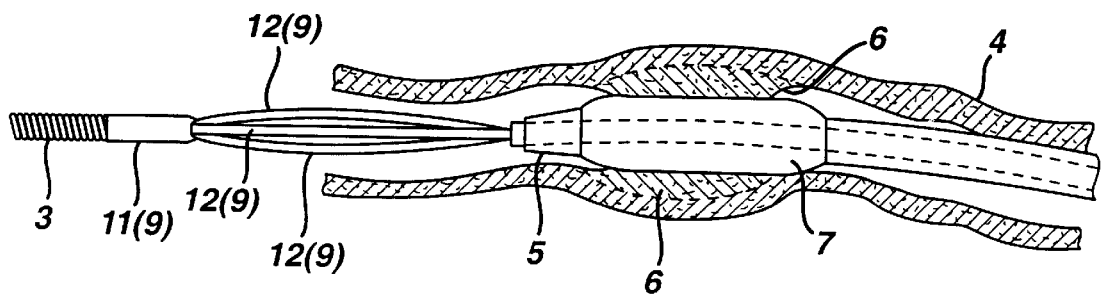

As shown in the FIG. 3(b), the switch 25 is closed to supply the electric power to the rod-shaped portion 12, and accordingly the rod-shaped portion 12 is warmed so as to curve outwardly in the radius direction of the cylindrical portion 11. The narrow portion 6 is preliminarily distended by the rod-shaped portion 12 being curved.

Subsequently, as shown in the FIG. 3(c), the guide-wire is gently inserted into a deeper position in the blood vessel 4. The balloon-tip catheter 5 is then guided along and slipped into a space in the blood vessel 4 defined by the curved rod-shaped portion 12. A balloon of the balloon-tip catheter 5 is enlarged to maintain the space. In this embodiment, nearly blocked portions in the blood vessel 4 can be distended as described above. Therefore, the balloon-tip catheter 5 following the guide-wire 1 can be easily passed therethrough, and an open procedure for distending the narrow portion 6 in the blood vessel 4 can be easily and immediately carried out.

Figure 4:
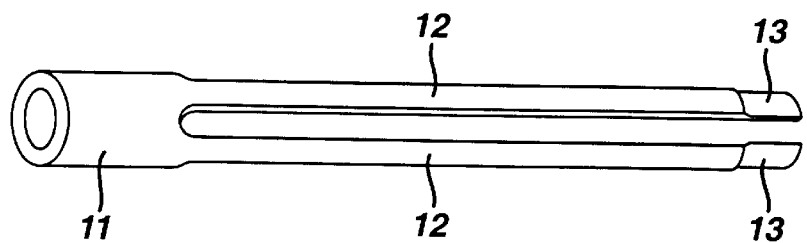
FIG. 4 is a general perspective view for explaining a method for manufacturing the distending portion of the guide-wire as the insertion instrument shown in FIGS. 1(a) to 1(c), 2(a) to 2(c) and 3(a) to 3(c)

A method of manufacturing the distending portion of the insertion instrument body shown in the FIGS. 1 to 3 will be explained hereinafter with reference to the FIG. 4. At first, a cylindrical body having a small radius is made from the shape-memory material such as alloys. Grooves extending in an axial direction of the cylindrical body are formed at constant intervals in a circumferential direction of the cylindrical body to produce a plurality of rod-shaped portions 12 defined between the grooves. A method of forming the grooves may be a wire cut electric spark machining method or well-known micro-machining methods such as a laser beam machining method, a dry-type etching method, a wet-type etching method or electronic beam method. In forming the grooves, it is necessary to leave one end of the cylindrical body as the cylindrical portion 11. In the FIG. 4, only one end of the cylindrical body is left as the cylindrical portion 11. (Of course, both ends of the cylindrical body may be left as the cylindrical portion 11.)

The cylindrical portion 11 supports the plurality of the rod-shaped portions 12 arranged in the circumferential direction thereof, and assists in the fixation of the metallic core portion 2 to the rod-shaped portion 12. Only the rod-shaped portions 12 are warmed to a required temperature so that the rod-shaped portions 12 memorize an original shape displaced in an outwardly radial direction of the cylindrical portion 11 above the required temperature. The distending portion 9 thus obtained is fixed at the distal end of the metallic core portion 2 by a variety of fixing methods such as the caulking method and so on to obtain a guide-wire as an insertion instrument body according to the present invention. "Outward radial direction" of the cylindrical portion 11 means an intersecting direction with respect to the longitudinal direction of the metallic core portion 2 when the distending portion 9 is fixed to the metallic core portion 2 to obtain the required guidewire.

In this embodiment, the cylindrical portion 11 supports the cantilever rod-shaped portions 12. As explained in the method of manufacturing the distending portion above, the plurality of rod-shaped portions 12 may be arranged between a pair of the cylindrical portions 11. The plurality of rod-shaped portions 12 may also be arranged between both ends of the cylindrical portion 11. Furthermore, while the number of rod-shaped portion 12 according to the embodiment is four, the number thereof in the present invention is not limited to this many.

Figure 5:
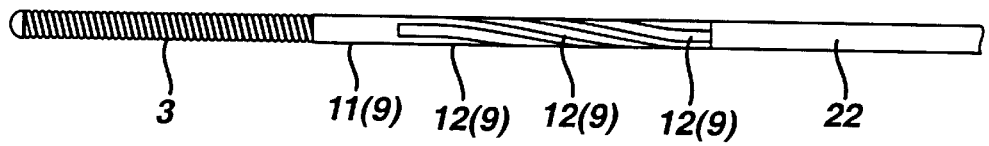
FIG. 5 is a front view showing a distal end of the guide-wire as a second embodiment of the insertion instrument of the present invention.
Figure 6:
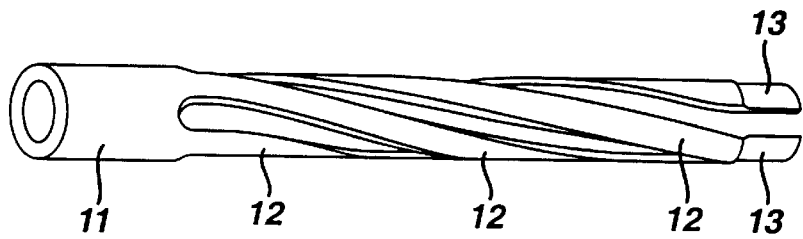
FIG. 6 is a general perspective view showing a distending portion in the guide-wire shown in the FIG. 5.

FIG. 5 is a front view showing a distal end of the guide-wire as an embodiment 2 of the insertion instrument of the present invention. FIG. 6 is a general perspective view showing a distending portion in the guide-wire shown in the FIG. 5. In this embodiment, the common elements in both the embodiments 1 and 2 are represented by the same reference numerals.

A feature of embodiment 2 is that the rod-shaped portion 12 is not a straight member but is helical. Namely, the rod-shaped portion 12 extends in an axial direction of the cylindrical portion 11 in the embodiment 1. On the other hand, the rod-shaped portion 12 of the present embodiment 2 extends in an intersecting direction with respect to the axial direction of the cylindrical portion 11 as shown in the FIG. 4. The helical rod-shaped portion 12 can be easily produced by forming the grooves at the cylindrical body rotated in the circumferential direction of the cylindrical body by using the above micromachining method such as the wire cut electric spark machining method or the laser beam machining method. According to the embodiment, the guide-wire can be easily inserted into the lumen in vivo by rotating the guide-wire along the helical groove, as if it were a screw.

Figure 7:
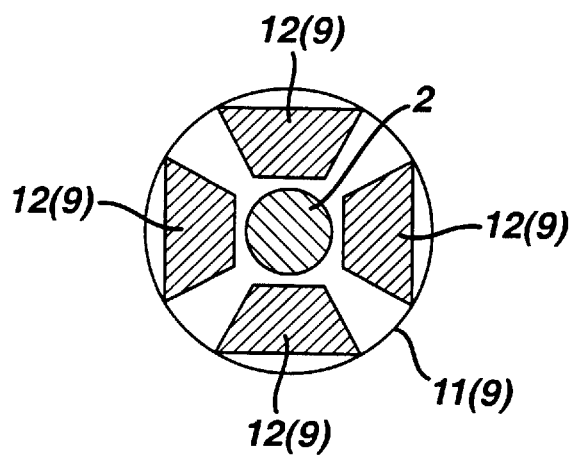
FIG. 7 is a cross sectional view showing an alternative embodiment of the distending portion in the first or second embodiment according to the present invention.

FIG. 7 is a cross sectional view showing an alternative embodiment of the distending portion in the embodiment 1 or 2 according to the present invention. The alternative embodiment has the same essential elements as the embodiments 1 and 2. A feature of the alternative is that an outer apex of the distending portion has a sharp angle. The sharp apex is exposed from the space defined by the outer surface of the cylindrical portion 11 above the transforming temperature.

According to the alternative embodiment, the sharp apex of the rod-shaped portion 12 can scrape projecting pathological changes produced at a narrow portion 6. Namely, when the insertion instrument body 8 inserted into the narrow portion 6 of the blood vessel 4 is curved above the transforming temperature, it is rotated in the circumferential direction of the cylindrical portion 11. Tissue scraped by the insertion instrument body 8 is kept in a space defined between the metallic core portion 2 and the plurality of the rod-shaped portions 12, and is removed from of the patient's body.

Figure 8:
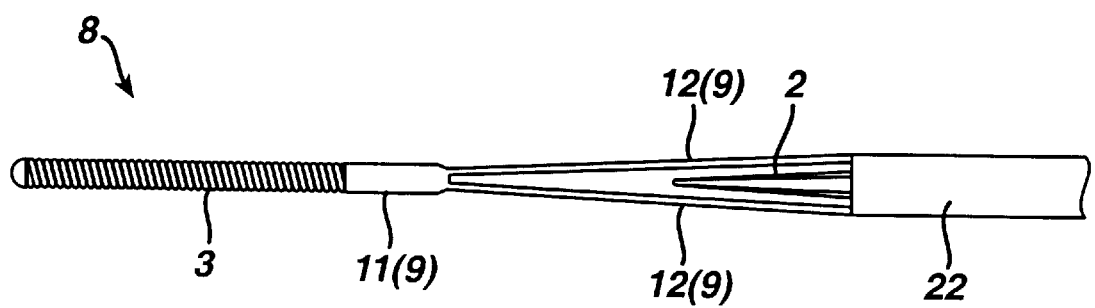
FIG. 8 is a front view showing a distal end of the guide-wire as a third embodiment of the insertion instrument of the present invention.

FIG. 8 is a front view showing a distal end of the guide-wire as an embodiment 3 of the insertion instrument of the present invention. The embodiment has the same essential elements as the embodiments described above. A feature of embodiment 3 is that the distal end of the guide-wire to be inserted into the lumen in vivo is tapered. Namely, the metallic core portion 3 does not extend fully to the distal end of the insertion instrument body 8. The outer diameters of the cylindrical portion 11 and the coil spring portion 3 are also smaller than that of the metallic core portion 2. Therefore, the insertion instrument body 8 as a guide-wire can pass through the narrow portion 6 of the blood vessel 4. Since the rod-shaped portions 12 can be curved outwardly after insertion of the guide-wire into the narrow portion 6, the following balloon-tip catheter 5 can proceed smoothly to the narrow portion 6.

The fourth through sixth embodiments of an insertion instrument body according to the present invention will be explained hereinafter with reference to FIGS. 9 to 11. In these embodiments, the following points are different from the embodiments 1 to 3 as described above. A rod-shaped body 12 memorizing the original shape described above constitutes the distending portion 9. The rod-shaped body 12 is arranged in a longitudinal direction of the metallic core portion 2, and is directly fixed at an outer face of the metallic core portion 2. In the FIGS. 9 to 11, a dotted line denotes the original shape to which the rod-shaped body 12 returns above the transforming temperature. Each embodiment will be explained hereinafter.

Figure 9:
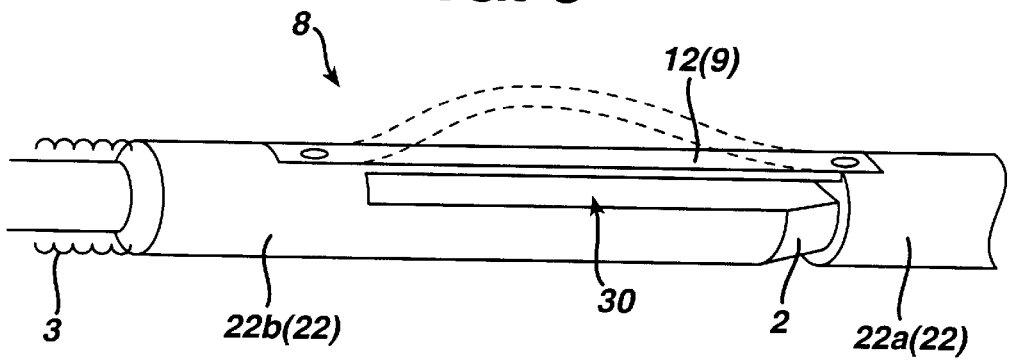
FIG. 9 is a general perspective view showing a distal end of the guide-wire as a fourth embodiment of the insertion instrument of the present invention.

The FIG. 9 is a general perspective view showing a distal end of the guide-wire as a fourth embodiment of the insertion instrument of the present invention. In this embodiment, a recess 30 is formed at the conductive sleeve 22 so as to expose partially an outer face of the metallic core portion 2. The rod-shaped body 12 is arranged so as to extend across the recess 30, and both ends of the rod-shaped body 12 are fixed to an outer face of the conductive sleeve 22 by using fixing methods such as a spot welding method.

Here, the right sleeve 22a is electrically insulated from the left sleeve 22b via the recess 30. In the FIG. 9, the right sleeve 22a is electrically insulated from the metallic core portion 2 positioned inside the sleeve 22a. The left of the sleeve 22b is electrically connected with the metallic core portion 2 inside the right sleeve 22a. In this embodiment, an electric circuit of the power supply means 10 is constituted of the right sleeve 22a, the rodshaped portion 12, the left sleeve 22b, the metallic core portion 2, the power source and the switch (both not shown), made by conventional means.

Figure 10:
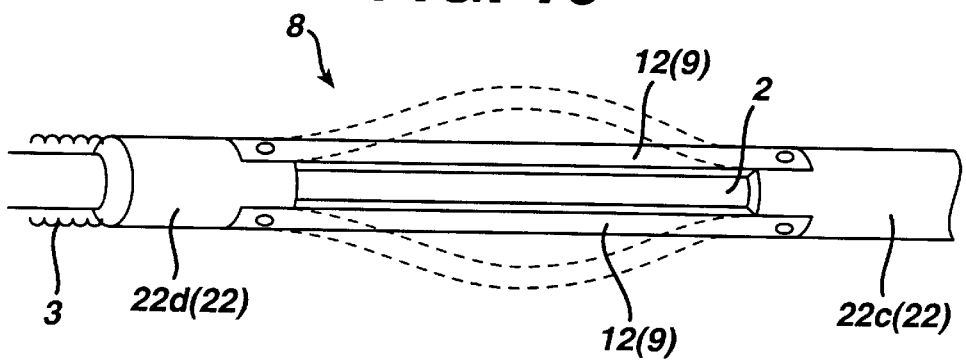
FIG. 10 is a general perspective view showing a distal end of the guide-wire as a fifth embodiment of the insertion instrument of the present invention.

FIG. 10 is a general perspective view showing a distal end of the guide-wire as a fifth embodiment of the insertion instrument of the present invention. In this embodiment, the conductive sleeve 22c is removed from the conductive sleeve 22d so that the metallic core portion 2 is exposed by a required length, and a plurality of the rod-shaped portions 12 are arranged so as to join both sleeves 22c and 22d. Both ends of the rod-shaped portion 12 are fixed to respective outer faces of the sleeves 22c and 22d by using fixing methods such as a spot welding method.

In this case, the sleeve 22c is electrically insulated from the sleeve 22d. In the FIG. 10, the right sleeve 22c is electrically insulated from the metallic core portion 2 positioned inside the right sleeve 22c. On the other hand, the left sleeve 22d is electrically connected with the metallic core portion 2. Namely, an electric circuit of the power supply means 10 is constituted of the right sleeve 22c, the rod-shaped portions 12, the left sleeve 22d, the metallic core portion 2, the power source and switch (not shown).

Figure 11:
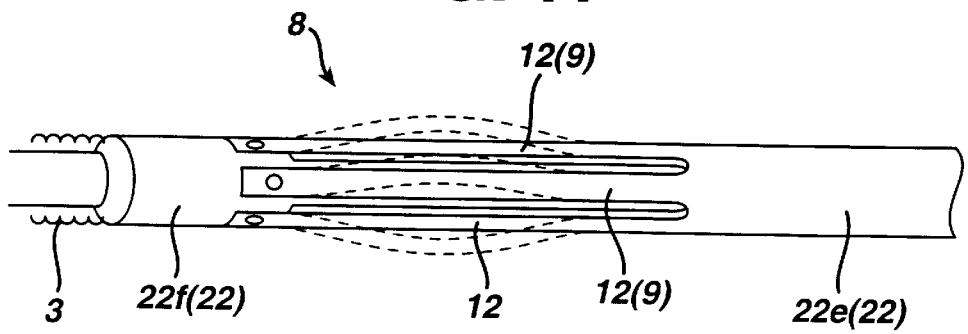
FIG. 11 is a general perspective view showing a distal end of the guide-wire as a sixth embodiment of the insertion instrument of the present invention.

FIG. 11 is a general perspective view showing a distal end of the guide-wire as a sixth embodiment of the insertion instrument of the present invention. This embodiment is the same as the embodiment 5, except for the following points. Namely, one end of the rod-shaped portion 12 is fixed to the left sleeve 22f by using fixing methods such as the spot welding method, and the other end of the rod-shaped portion 12 is integrally formed in the right sleeve 22e.

In this case, the sleeve 22e is electrically insulated from the sleeve 22f. In the FIG. 11, the right sleeve 22e is electrically insulated from the metallic core portion 2 positioned inside the right sleeve 22f. On the other hand, the left sleeve 22f is electrically connected with the metallic core portion 2. Namely, an electric circuit of the power supply means 10 is constituted of the right sleeve 22e, the rod-shaped portions 12 integrally formed therein, the left sleeve 22f, the metallic core portion 2, the power source and the switch.

As described above, each rod-shaped portion 12 of the insertion instrument body 9 is exposed against the lumen in vivo. The rod-shaped portions 12 are totally covered with at least one protective sleeve. The protective sleeve is preferably made from the flexible material like the sleeves 22 described above.

As described above, in the present invention, a distending portion of the shape-memory material arranged on the outer face of the distal end of the longitudinal base portion can be heated above the transforming temperature of the shape-memory material by the power supply means. The rod-shaped portion above the transforming temperature can immediately and easily distend the narrow portion in the lumen in vivo so that the stream of a fluid such as blood can be improved. It is accordingly possible to promptly perform a surgical operation for removing a pathological change produced in a narrow portion in the blood vessel.

In the surgical operation, the pathological change projected inwardly in the lumen can be cut out by rotating the distending portion outwardly distended about the axis of the insertion instrument body according to the invention. Since the shape of the distending portion returns to a straight shape below the transforming temperature, a tissue cut out by the distending portions can be kept in the distending portions of the insertion instrument body. The tissue can be further removed by pulling the insertion instrument body as a guide-wire out of the patient's body. By using the insertion instrument body according to the present invention, interventional operation can be shortened.

What is claimed is:

1. An insertion instrument body to be inserted into a lumen comprising:
   a longitudinal base portion insertable into the lumen;
   a distending portion arranged on an outer face of the distal end of said base portion, wherein said distending portion extends along a longitudinal direction of said base portion and is at least partially formed of a shape-memory material having a transforming temperature; and
   a power supply means for heating said distending portion to a temperature above the transforming temperature; and wherein the base portion is formed of a conductive material, and a conductive sleeve is arranged on an outer face of the base portion through an electrical insulating layer.

2. The insertion instrument body of claim 1 wherein the distending portion is supported on a peripheral part of a cylindrical portion.

3. The insertion instrument body of claim 2 wherein a cross section of the distending portion extends transversely with respect to the longitudinal areas the distending portion.

4. The insertion instrument body of claim 3 wherein in an outer apex of the distending portion has a sharp angle.

5. The insertion instrument body of claim 3 wherein the conductive sleeve is divided into two parts in a longitudinal direction of the base portion; the distending portion connects the divided conductive sleeves in the longitudinal direction of the base portion to join both sleeves; one of the sleeves is electrically connected with the base portion, and the other is electrically insulated from the base portion.

6. The insertion instrument body of claim 2 wherein the distending portion is arranged on the peripheral part of the cylindrical portion at regular intervals.

7. The insertion instrument body of claim 2 wherein the distending portion spirally extends from one of the peripheral parts of the cylindrical portion.

8. The insertion instrument body of claim 1, wherein there are a plurality of distending portions.

9. The insertion instrument body of claim 1 wherein the distending portion is plate-shaped or wire-shaped.

10. The insertion instrument body of claim 1 wherein the distending portion is arranged on an outer face of the distal end of the base portion.

11. The insertion instrument body of claim 1 wherein the distending portion is integrally formed therein.

12. The insertion instrument body of claim 1 wherein the distal end to be inserted into the lumen is tapered.

13. The insertion instrument body of claim 1 wherein the distending portions are accommodated in a space defined by an outer face of the cylindrical portion.

* * * * *